Figure 1:
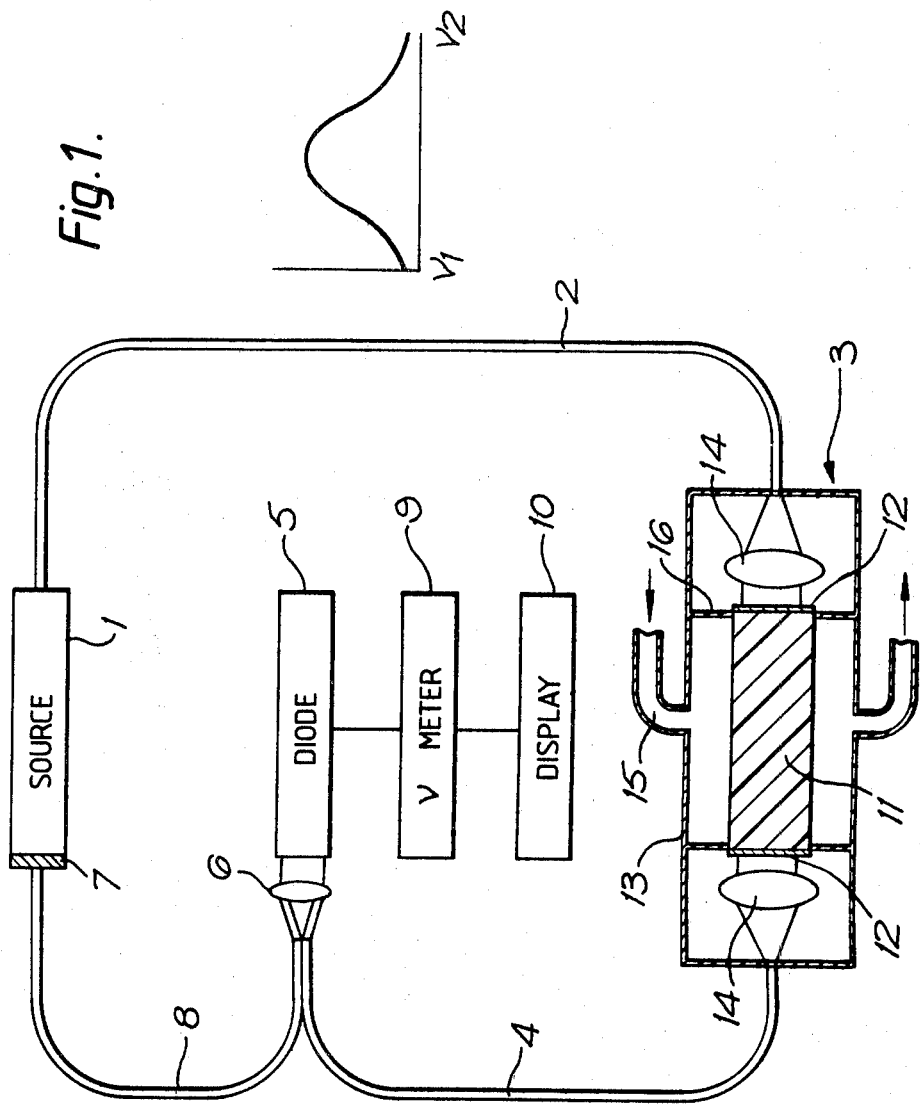

United States Patent [19]

Murray et al.

[11] 4,417,815

[45] Nov. 29, 1983

[54] MEASURING APPARATUS

[75] Inventors: Robert T. Murray, Helsby, England; Daniel J. Bradley, Dublin, Ireland

[73] Assignee: Imperial Chemical Industries PLC, London, England

[21] Appl. No.: 328,710

[22] Filed: Dec. 8, 1981

[30] Foreign Application Priority Data

Dec. 17, 1980 [GB] United Kingdom ............... 8040393

[51] Int. Cl.³ .................................................. G01B 9/02
[52] U.S. Cl. ..................................... 356/349; 356/352
[58] Field of Search ....................... 356/346, 349, 352; 436/152, 159, 164; 250/231 P

[56] References Cited

U.S. PATENT DOCUMENTS 4,355,898 10/1982 Dakin ................................. 356/346

FOREIGN PATENT DOCUMENTS 13974 8/1980 European Pat. Off. .

OTHER PUBLICATIONS

Henderson, "Interferometry of the E Corona", *Applied Optics*, vol. 9, No. 12, pp. 2635-2642, Dec. 1970.

*Primary Examiner*—William L. Sikes
*Assistant Examiner*—Matthew W. Koren
*Attorney, Agent, or Firm*—Cushman, Darby & Cushman

[57] ABSTRACT

Apparatus for measuring or detecting changes in a variety of physical or chemical parameters comprises an interferometer having a transmission frequency variable over a range of frequencies as a function of changes in the parameter. The transmission frequency is measured by beating with a coherent reference frequency.

10 Claims, 5 Drawing Figures

MEASURING APPARATUS

This invention relates to apparatus for measuring or detecting changes in physical or chemical parameters using optical interference techniques.

According to the present invention, an apparatus for measuring or detecting changes in a physical or chemical parameter comprises a light source, an interferometer having variable interference means positioned to receive light from the source and to transmit a portion of that light at a discrete frequency which is variable over a range of frequencies within the source bandwidth, means for applying the parameter to the interference means thereby to vary the transmission frequency as a function of changes in the parameter, means for beating the transmitted frequency with a reference frequency taken coherently from the same light source, and detection means for measuring or detecting changes in the beat frequency thereby produced.

The light source may cover a finite bandwidth anywhere within that portion of the spectrum which is readily transmitted by optical fibres. At present optical fibres can be obtained which can transmit all the visible light, the near ultra-violet, and extend well into the infra-red. As will be realised, the light source bandwidth must be substantially broader than the resolution of the interferometer in order that the latter may provide a range of transmitted frequencies within that bandwidth. On the other hand, where the source bandwidth is greater than the spectral range of the interferometer, more than one discrete frequency may be transmitted, leading to a plurality of beat frequencies. This makes complex analysis of the beats necessary, and loses much of the simplicity of operation which is otherwise possible.

The spectral range of an interferometer is the separation of any two transmitted frequencies differing by one order of interference, i.e. the spectral range is the maximum value of $\delta\nu$ which is sufficiently small for the nth order of interference at frequency $\nu$ not to overlap with the $(n+1)$th order of interference at frequency $(\nu+\delta\nu)$. A preferred apparatus is one wherein the total bandwidth of light reaching the detector after passing through the interferometer, is equal to or less than the spectral range of the interferometer, thereby to produce only a single beat frequency at a time. Where a broad band light source is used, the bandwidth can be restricted by passing the beam through filters of the appropriate bandwidth. However, it is generally preferred to restrict the bandwidth at source, such as by using a source which does itself emit light having a bandwidth equal to or less than the spectral bandwidth of the interferometer.

Suitable light sources include gas lasers and laser diodes which fall within the above criteria. Some of these may also produce light at frequencies other than their dominant frequencies, but at much lower intensities.

Where these can also produce beat frequencies, they may be filtered out or the sensitivity of the apparatus reduced until they become undetectable. However, in practice, any beat frequency due to these stray lines will generally be so high as to be undetected.

The preferred interferometer is a Fabry-Perot interferometer comprising partially reflective parallel layers separated by a transparent spacing layer whose refractive index or thickness is variable with variation in the parameter to be measured. The resolving power depends on the reflectivity of the reflective layers. The greater the reflectivity, the greater is the resolving power, (and hence the narrower may be the source bandwidth) and hence the accuracy of the frequency shift measurement; but this can only be achieved with a reduction in the intensity of the transmitted radiation. The spectral range of a Fabry-Perot interferometer is given by the formula:

$$\Delta\nu = C/2\mu t$$

where $\mu$ is the refractive index and t is the thickness of the spacing layer. Hence the thicker the spacing layer, the smaller is the spectral range, and thus also the source bandwidth, which can be used. The parameter to be measured is applied to the interferometer so as to vary the thickness or refractive index of the spacing layer as a function of variations in the parameter. While varying one of those two variables in the interferometer, the other may of course be varied at the same time either intentionally or because it is unavoidable, the overall effect of which may be enhancement or reduction of the effect due to only one of the variables.

The nature of the spacing layer and the manner in which the parameter is applied depend very much on the parameter to be measured. Thus for example, the spacing layer may be a transparent solid block with parallel faces coated to provide the partially reflective layers. Changes in temperature or pressure may vary the optical path length and hence cause a change in the transmission frequency. A hollow block may be used in a similar manner but the relative contributions of changes in refractive index and thickness respectively with changes in the applied parameter, will generally be different from those of a solid block.

Where other requirements (e.g. spectral range) permit, a more generally versatile interferometer is one in which the spacing layer is a hollow cell with means for introducing and removing a fluid. This may be used for measuring such parameters as temperature, pressure and chemical composition by using a fluid whose refractive index can change with changes in such parameters. Alternatively the interferometer may be one wherein the hollow cell is connected to the reflective layers such that variations in the pressure of fluid in the cell cause variations in the spacing of the reflective layers. This may be used to measure not only pressure, but indirectly other parameters also, where such parameters (e.g. temperature) may be used to vary the pressure of the fluid in the cell.

Although capable of obtaining quantitative results, the apparatus may be used simply for detecting a change in a parameter, and operating an alarm or initiating a further series of events when such a change is detected. For example an effluent gas stream may be monitored for the presence of a particular poison gas having a different refractive index or behaving differently to a selective catalyst as described in more detail hereinafter. For such purposes simple detection of a change in beat frequency from a norm by a predetermined amount, may be all that is required.

The apparatus can readily be adapted for the measurement or detection of changes in a wide variety of physical and chemical parameters. No electrical power is required at its point of measurement and its ability to use fibre optics for communicating with distant control centres enables inherently safe process control to be achieved. As such it is particularly advantageous in petroleum plants and other flame-free hazard areas. It is also useful in enabling information to be obtained, free from electrical interference.

The apparatus is particularly useful for monitoring a gas stream for the presence of a specific gas which is reactable in the presence of a catalyst with the evolution or absorption of heat. The apparatus is adapted for this use by employing an interferometer which is sensitive to changes in temperature, and locating it in thermal contact with a mass of the catalyst, so that in turn it becomes sensitive to any specific gas changing the temperature on meeting the catalyst.

We prefer to set up such apparatus by providing a conduit having an inlet and an outlet to enable the gas stream to be passed through the conduit, the sensitive interferometer with its catalyst being located within the conduit, the conduit also being provided with a reference interferometer upstream of the sensitive interferometer wherein the reference interferometer is substantially the same as the sensitive interferometer except that it is not in contact with any of the catalyst. Light from the source is then supplied separately to each interferometer, and their transmitted portions thereafter combined to produce the beats. The reference interferometer in this application of the apparatus not only provides a narrow frequency band to give strong beats, but it also reacts to changes in ambient temperatures and changes in the temperature of the gas stream being supplied to the conduit, in essentially the same manner as the sensitive interferometer. Hence the beat frequencies remain substantially unchanged by such extraneous temperature changes.

The apparatus is not, however, restricted to remote sensing applications, and can, in fact, also provide a range of self-contained analytical sensors having a variety of laboratory and chemical plant uses.

Figure 2:
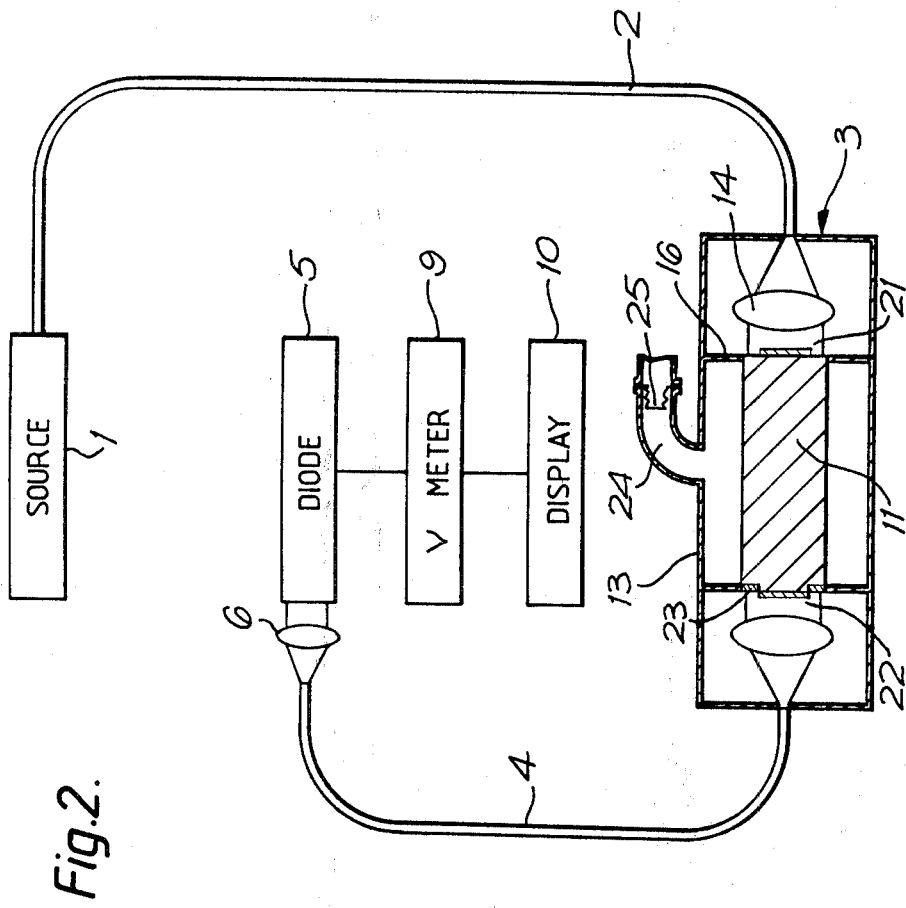
Figure 3:
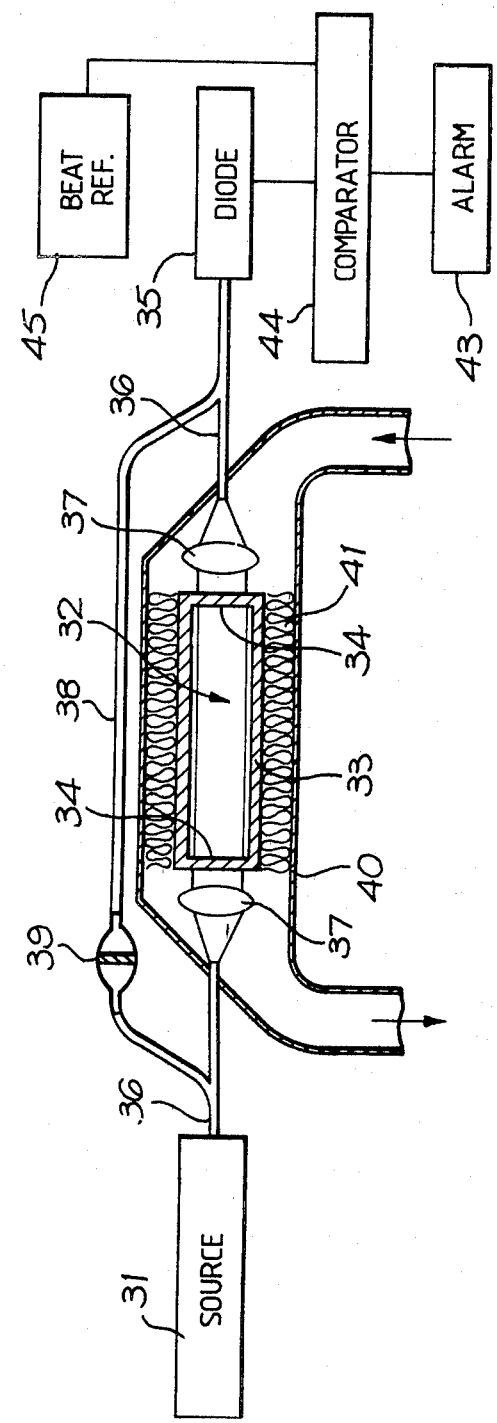
Figure 4:
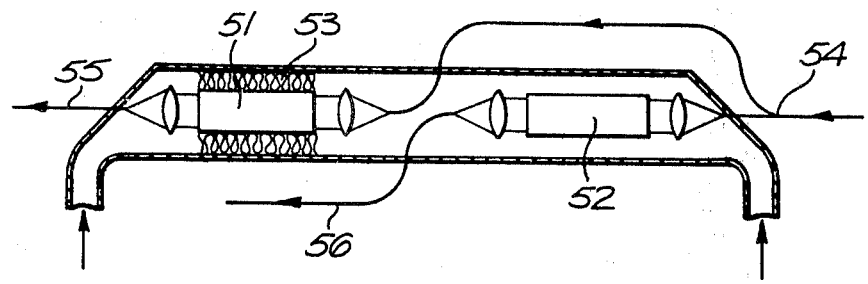
Figure 5:
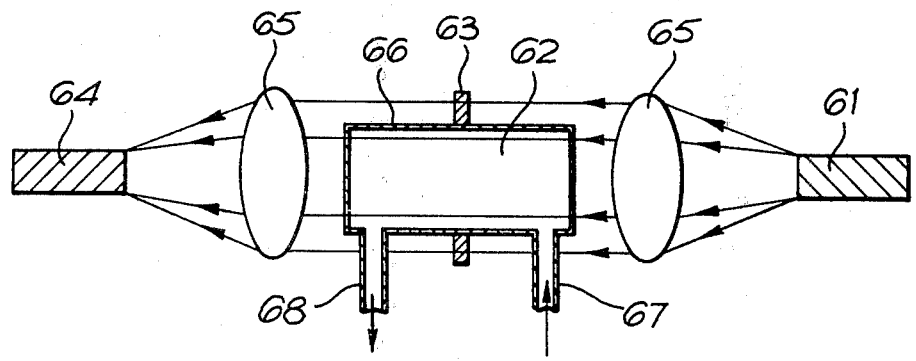

The invention is illustrated by reference to specific embodiments thereof shown in the accompanying drawings, in which FIG. 1 is a diagrammatic representation of an apparatus having an interferometer designed for measuring the temperature of a gas flowing along a pipe, FIG. 2 is a similar representation of another apparatus using an alternative system for obtaining beating with a coherent reference frequency, and using an interferometer designed for measuring pressure, FIG. 3 is a diagrammatic section through an interferometer designed for detecting specific gases in a gas stream, FIG. 4 shows a device similar to that shown in FIG. 3 modified to compensate for temperature variations in the gas stream, and FIG. 5 is a diagrammatic section through an alternative analytical sensor for detecting the presence of a gas, and for measuring its concentration if so required.

In the apparatus of FIG. 1, a light source 1 emits radiation which is transmitted by an optical fibre 2 to an interferometer 3. Light emerging from the interferometer is focussed onto one end of an optical fibre 4 which carries it towards a photodiode 5, onto which it is focussed by a lens 6. A reference sample of light from the source passes through a filter 7 and is carried by a further optical fibre 8, to be focussed onto the photodiode by the same lens 6 as that used for the light from the interferometer, in such a way as to maximise overlap. The two optical paths are provided with additional elements (not shown) as necessary to maintain coherency of the two samples of light being focussed together onto the diode. The latter is connected electrically to a frequency meter 9 and thence to a display 10.

The interferometer 3 is of the Fabry Perot type, comprising a solid block 11 having parallel end faces 12 coated to about 95% reflectivity. This is mounted in a case 13 having windows and collimating lenses 14 to direct incoming light from one optical fibre 2 onto the interferometer, and to focus the emerging light onto the other adjacent fibre 4 for transmission to the diode. The case is let into a pipe 15 through which travels the gas whose temperature is to be measured, and the block is supported in the case by bulkheads 16 which form a gas-tight seal between the block and the case.

The various samples of light travelling along the optical fibres during operation of the apparatus have different intensity profiles with frequency. These are sketched graphically adjacent to the optical fibres to which they relate. Thus light travelling along the optical fibre 2 interconnecting the source 1 and interferometer 3 has a finite bandwidth $\nu_1 - \nu_2$. In the interferometer the light is multiply reflected within the block 11 and emerges along the axis as a single discrete frequency $\nu_x$ which lies within the band $\nu_1 - \nu_2$. The bandwidth of the emerging light is a function of the reflectivity of the coated end faces and the length of the etalon. In this apparatus the faces have been given high reflectivity to obtain an emergent light which is substantially monochromatic by comparison with the source radiation. This is obtained at the expense of intensity and the filter 7 is designed to provide a reference beam which is not only substantially monochromatic, with a frequency of $\nu_o$, but which is also attenuated to approximately the same intensity as the light emerging from the interferometer.

Gas flowing along the pipe passes through the case 13 where it contacts the block 11 and maintains the latter at the same temperature as the gas itself. Any changes in the temperature of the gas cause corresponding changes in the temperature of the block whose dimensions and refractive index change as a direct result. The optical path through the interferometer, and hence the frequency of the transmitted radiation, is therefore varied as a function of changes in the temperature of the gas. The bulkheads 16 are provided to prevent the gas from entering the optical path through the system, so that any changes are due to the temperature changes and not to any refractive index changes within the gas itself.

The transmitted light is combined with the reference sample on the surface of the photodiode and, being coherent, they interfere. The are, however, very close in frequency and so produce a beat frequency which is sufficiently slow to be resolved by the photodiode. The rate of beating is then measured electronically by the frequency meter and the result made accessible by a visual display unit 10. This display unit could equally well be a pen and chart recorder or a digital display, or indeed may be replaced by or include, feed back to adjust the temperature control when the temperature varies from a preset value by an unacceptable amount.

The apparatus shown in FIG. 2 has several features in common with that of FIG. 1, and so like numbering has been used for like parts where appropriate. Thus a laser source 1 emits radiation having a bandwidth of $(\nu_2 - \nu_1)$, which is carried along an optical fibre 2 to an interferometer 3. It is then collimated onto a solid transparent block 11, and the axial emergent radiation is focussed onto a second optical fibre 4 which carries it to a photodiode 5. Output from the diode goes to a frequency meter 9 and thence to a display 10.

This example does differ from the previous, however, in that no further sample of the source radiation is provided separately. Instead, only a portion 21 of the inlet end of the block is reflectively coated with a corresponding portion 22 of the exit end likewise coated. Around the coated position of the exit end is also provided an annular transmission filter 23. Thus with a source bandwidth of $\nu_1$ to $\nu_2$ as before, the central portion of the block transmits at a discrete frequency $\nu_x$ while the surrounding annulus transmits at a frequency of $\nu_o$, the areas being adjusted such that the transmitted frequencies emerge at a similar order of magnitude. These are focussed by a lens 14 onto the end of the second optical fibre 4, such lens being preferably of graded index rod construction. Being coherent, they will beat as before, but in this case, the sample and reference frequencies are combined before being carried along the second optical fibre to the diode. This ensures that they are combined within the coherence length of the radiation without any need for additional fibre lengths or delay loops.

The other change incorporated into FIG. 2 is the provision of only a single port 24 communicating with the case in order to convey pressure through a substantially stationary fluid from external equipment whose internal pressure is to be measured. As a safety measure, this embodiment is also shown with an isolating diaphragm 25 located between the apparatus and the fluid whose pressure is to be measured, in order to avoid contamination with that fluid where the latter is corrosive or perhaps sensitive to the materials or radiation used in the apparatus.

The apparatus of FIG. 3 was designed to detect in a stream of oxygen, gases combustible in the presence of a catalyst; but it is equally applicable to the detection of other gases which react or decompose spontaneously in the presence of a catalyst, with the evolution or absorption of heat.

The optics of this apparatus consist essentially of a light source 31, a Fabry Perot interferometer 32 comprising a transparent hollow block 33 partially coated on its internal parallel end faces 34 to a reflectivity of about 95% for each face, a photodiode 35, optical fibres 36, for carrying the light from the source to the interferometer and thence to the diode via lens systems 37 and a bypass fibre 38 carrying an interference filter 39 of pass frequency $\nu_o$. The interferometer is enclosed in a case 40 having inlet and outlet through which gas can flow, and a porous mass of catalyst 41 is located around the transparent block. Output from the diode is fed to an alarm 43 via a comparator 44 connected to a reference 45.

In use, gas (oxygen) is passed through the casing at a constant temperature, and when there are none of the combustible gases present, the temperature of the block remains at the predetermined constant temperature. The reference 45 is then set to the same frequency as the beat frequency. When a combustible gas is present and the catalyst induces combustion, the exotherm heats the hollow tube and moves apart the coated faces. This changes the transmission frequency, and hence the beat frequency. When the latter departs from the reference by more than a predetermined amount, the alarm is triggered.

The embodiment of FIG. 3 is difficult to use for detecting small quantities of combustible gases, as temperature variations in the ingoing gas stream can mask any small temperature rise due to combustion. In FIG. 4 two similar Fabry-Perot interferometers 51, 52 are placed in the gas stream, one 51 being coated with catalyst 53, the other not. These are shown in close tandem formation, but that need not be so provided both are in temperature equilibrium with the gas, and provided that the heat generated by reaction in the vicinity of the catalyst does not affect the temperature of the reference interferometer 52. Light from a source (not shown) is piped into the system via an optical fibre to a Y junction 54, where it is divided into two roughly equal portions. These are directed onto the two interferometers, one portion each, by collimating lenses. The radiation emerging from the two interferometers is focussed onto two equal optical fibres 55, 56 to be carried away, combined and applied as a beat frequency to a photodiode or other detector, substantially as shown in FIG. 1.

Where the two interferometers are indentical, the emerging frequencies will be the same when no reaction takes place on the catalyst. However, the two emerging frequencies need not be identical, although they do need to be sufficiently close to fall within the bandwidth of the source and to produce a beat frequency measurable by the detector used. When a reaction occurs and changes the temperature of the interferometer and hence of the transmitted frequency, measurement of the change in the beat frequency gives a measure of the amount of combustible gas in the carrier stream. As the temperature of the carrier stream varies, the two interferometers are equally affected, and the beat frequency should not change on that account.

Apparatus showing in FIG. 5 was designed as a lightweight portable gas detector, which could be connected into a gas stream or sample the atmosphere, to detect certin gases or to measure their concentration. It has a source 61 producing radiation which is divided, part going through an interferometer 62 and the remainder bypassing the interferometer, either by simply passing around the interferometer as shown, or by following a separate guided path. In both cases this remainder passes through a stable filter 63 to provide a constant reference frequency. Both the transmitted beam and the reference beam are received on the surface of a frequency responsive detector 64 to provide a beat frequency in like manner to the previous example, the optical system again consisting essentially of lenses 65 for collimating and focussing the radiation respectively. The interferometer consists of a hollow cell 66 having inlet 67 and outlet 68 for connection to external equipment containing the gas to be analysed, or it may be provided with a simple metering pump when its purpose is to sample the air.

As with the other examples, when the gas to be detected is present, the transmission frequency changes. However, in contrast to the apparatus of FIG. 4 which relied on reactivity of the gases to give a temperature change, the present apparatus of FIG. 5 uses a change of refractive index when the appropriate gas is present. This makes use of the very rapid variation in refractive index adjacent to a resonant frequency of the gas molecules, and the length of the cell is selected such that its transmission frequency corresponds to an absorption frequency of the gas to be detected, with the source frequency band spanning the absorption frequency. The cells may be specifically designed for a particular gas, or a tuneable etalon may be used. Radiation bands within the near infra-red provide absorption frequencies for most gases.

Where the source spectrum has a sufficiently sharply peaked spectrum, beating might be obtainable in FIGS. 2 and 5 without the provision of a filter for sharpening the reference frequency ($\nu_o$), when the intensities are adjusted (e.g. by attenuators or by using suitable transmissive areas) to be at least approximately the same. However, in order to produce stronger beats, we prefer to use a sharply defined reference frequency as indicated in FIG. 1, and to produce this by passing a portion of the light from the source through a stable Fabry-Perot device or other stable interference filter which transmits at a frequency within the source bandwidth. This also has an advantage in that the selected reference frequency can be to one edge of the source waveband, thereby maximising the spread of frequencies which can be used effectively by the variable interferometer.

Each of the specific embodiments shown in the drawings, is a combination of several different features for most of which there are a number of alternatives. The specific embodiments have therefore been selected so as to illustrate as many of the more useful alternatives as possible in a reasonably small number of examples. Many of individual features are, however, interchangeable and may be selected to suit specific requirements. For example, the embodiment shown in FIG. 5 may be adapted for remote analysis or detection by incorporating fibre optics as shown in one of the other drawings. Similarly the interferometer of FIG. 1 may have a hollow etalon as shown in FIG. 3 to reduce its thermal mass, or a separate reference beam as shown in FIG. 1 may be used in the apparatus of FIG. 2 where particularly high pressures require such strong cases that passage of reference radiation through the apparatus becomes difficult to achieve.

What we claim is:

1. Apparatus for measuring or detecting changes in a physical or chemical parameter comprises:
a light source,
an interferometer having variable interference means positioned to receive light from the source and to transmit a portion of that light at a discrete frequency which is variable over a range of frequencies within the source bandwidth,
means for applying the parameter to the interference means thereby to vary the transmission frequency as a function of changes in the parameter,
means for beating the transmitted frequency with a reference frequency taken coherently from the same light source, and
detection means for measuring or detecting changes in the beat frequency thereby produced.

2. Apparatus as claimed in claim 1 wherein the total bandwidth of the light reaching the detector after passing through the interferometer is equal to or less than the spectral range of the interferometer thereby to produce only a single beat frequency at a time.

3. Apparatus as claimed in claim 2 wherein the source is one which emits light having a bandwidth equal to or less than the spectral bandwidth of the interferometer.

4. Apparatus as claimed in any one of the preceding claims wherein the reference frequency is obtained by passing a portion of the light from the source through a stable interference filter which transmits at a frequency within the source bandwidth.

5. Apparatus as claimed in claim 1 wherein the interferometer is a Fabry Perot interferometer comprising partially reflective parallel layers separated by a transparent spacing layer whose refractive index or thickness is variable with variations in the parameter.

6. Apparatus as claimed in claim 5 wherein the spacing layer is a transparent solid block with parallel faces coated to provide the reflective layers.

7. Apparatus as claimed in claim 5 wherein the spacing layer is a hollow cell with means for introducing and removing a fluid.

8. Apparatus as claimed in claim 7 wherein the hollow cell is connected to the reflective layers such that variations in the pressure of the fluid within the cell cause variations in the spacing of the reflective layers.

9. Apparatus as claimed in any one of claims 1 to 3 for measuring or detecting in a gas stream a specific gas reactable in the presence of a catalyst with the evolution or absorption of heat, wherein the interferometer is sensitive to changes in temperature and is in thermal contact with a mass of the catalyst.

10. Apparatus as claimed in claim 9 comprising a conduit having an inlet and an outlet to enable the gas stream to be passed through the conduit, the interferometer and catalyst in thermal contact with it being located within the conduit thereby to be sensitive to any of the specific gas within the stream flowing through the conduit, the conduit also being provided with a reference interferometer upstream of the sensitive interferometer, the reference interferometer being substantially the same as the sensitive interferometer except that it is not in contact with any of the catalyst, light from the source being supplied separately to each interferometer and their transmitted portion thereafter being combined to produce the beats.

* * * * *